United States Patent [19]
Casscells et al.

[11] Patent Number: 6,004,320
[45] Date of Patent: Dec. 21, 1999

[54] CLIP ON ELECTROCAUTERIZING SHEATH FOR ORTHOPEDIC SHAVE DEVICES

[75] Inventors: Christopher D. Casscells, Greenville, Del.; Ramiro L. Reyes, Union City; Hugh R. Sharkey, Woodside, both of Calif.

[73] Assignee: Oratec Interventions, Inc., Menlo Park, Calif.

[21] Appl. No.: 09/034,830

[22] Filed: Mar. 4, 1998

Related U.S. Application Data

[60] Provisional application No. 60/059,383, Sep. 19, 1997.

[51] Int. Cl.$^6$ .................................................. A61B 17/39
[52] U.S. Cl. .............................. 606/49; 606/50; 606/170; 606/180
[58] Field of Search ................................ 606/45, 46, 48, 606/49, 50, 170, 180, 41

[56] References Cited

U.S. PATENT DOCUMENTS

| | | | |
|---|---|---|---|
| 2,090,923 | 8/1937 | Wappler | 128/303.15 |
| 3,178,728 | 4/1965 | Christensen | 3/1 |
| 3,579,643 | 5/1971 | Morgan | 3/1 |
| 3,776,230 | 12/1973 | Neefe | 128/260 |

(List continued on next page.)

FOREIGN PATENT DOCUMENTS

| | | | |
|---|---|---|---|
| 0 257 116 A1 | 3/1988 | European Pat. Off. | A61N 1/36 |
| 0 274 705 A1 | 7/1988 | European Pat. Off. | A61M 23/00 |
| 0 479 482 A1 | 4/1992 | European Pat. Off. | A61B 17/39 |
| 0 521 595 A2 | 1/1993 | European Pat. Off. | A61M 25/01 |

(List continued on next page.)

OTHER PUBLICATIONS

Auhll, Richard A., "The Use of the Resectoscope in Gynecology." Biomedical Business International, Oct. 11, 1990, pp. 91–93.

Christian, C. et al., "Allograft Anterior Cruciate Ligament Reconstruction with Patellar Tendon: An Endoscopic Technique", *Operative Techniques in Sports Medicine*, vol. 1, No. 1, Jan. 1993, pp. 50–57.

(List continued on next page.)

*Primary Examiner*—Lee Cohen
*Attorney, Agent, or Firm*—David J. Weitz; Wilson Sonsini Goodrich & Rosati

[57] ABSTRACT

Disclosed is an integrated surgical and cauterizing apparatus, comprising a surgical instrument including a drive member, a cannula, and a tool, and the cannula attached at a proximal end to the drive member and defining at a distal end thereof an opening, and the tool including a shaft and a tip, and the shaft contained within he cannula and connecting the tip in the opening of the cannula to the drive member to produce a surgical motion of the tip; and a cauterizing instrument comprising at least one electrode, and a conductor, and at least one electrode affixed to the cannula adjacent to the distal end of the cannula and the conductor providing an electrical path from the at least one electrode for the application of electrical power to the at least one electrode to produce a cauterizing effect.

2 Claims, 8 Drawing Sheets

U.S. PATENT DOCUMENTS

| | | | |
|---|---|---|---|
| 3,856,015 | 12/1974 | Iglesias | 128/303.15 |
| 3,867,728 | 2/1975 | Substad et al. | 3/1 |
| 3,879,767 | 4/1975 | Substad | 3/1 |
| 3,886,600 | 6/1975 | Kahn et al. | 3/1 |
| 3,938,198 | 2/1976 | Kahn et al. | 3/1.912 |
| 3,945,375 | 3/1976 | Banko | 128/6 |
| 3,987,499 | 10/1976 | Scharbach et al. | 3/1.91 |
| 3,992,725 | 11/1976 | Homsy | 3/1 |
| 4,043,342 | 8/1977 | Morrison, Jr. | 128/303.14 |
| 4,085,466 | 4/1978 | Goodfellow et al. | 3/1.91 |
| 4,129,470 | 12/1978 | Homsy | 156/155 |
| 4,134,406 | 1/1979 | Iglesias | 128/303.15 |
| 4,224,696 | 9/1980 | Murray et al. | 3/1.911 |
| 4,224,697 | 9/1980 | Murray et al. | 3/1.911 |
| 4,326,529 | 4/1982 | Doss et al. | 128/303.1 |
| 4,344,193 | 8/1982 | Kenny | 3/1.911 |
| 4,362,160 | 12/1982 | Hiltebrandt | 128/303.15 |
| 4,375,220 | 3/1983 | Matvias | 128/804 |
| 4,381,007 | 4/1983 | Doss | 128/303.1 |
| 4,397,314 | 8/1983 | Vaguine | 128/399 |
| 4,476,862 | 10/1984 | Pao | 128/303.17 |
| 4,483,338 | 11/1984 | Bloom et al. | 128/303.13 |
| 4,517,965 | 5/1985 | Ellison | 128/20 |
| 4,517,975 | 5/1985 | Garito et al. | 128/303.13 |
| 4,590,934 | 5/1986 | Malis et al. | 128/303.14 |
| 4,593,691 | 6/1986 | Lindstrom et al. | 128/303.14 |
| 4,597,379 | 7/1986 | Kihn et al. | 128/1 R |
| 4,601,705 | 7/1986 | McCoy | 604/94 |
| 4,651,734 | 3/1987 | Doss et al. | 128/303.14 |
| 4,811,733 | 3/1989 | Borsanyi et al. | 128/303.14 |
| 4,815,462 | 3/1989 | Clark | 128/305 |
| 4,838,859 | 6/1989 | Strassmann | 604/95 |
| 4,873,976 | 10/1989 | Schreiber | 128/334 R |
| 4,894,063 | 1/1990 | Nashef | 623/13 |
| 4,895,148 | 1/1990 | Bays et al. | 606/213 |
| 4,907,585 | 3/1990 | Schachar | 606/28 |
| 4,907,589 | 3/1990 | Cosman | 606/34 |
| 4,920,978 | 5/1990 | Colvin . | |
| 4,924,865 | 5/1990 | Bays et al. | 606/77 |
| 4,944,727 | 7/1990 | McCoy | 604/95 |
| 4,950,234 | 8/1990 | Fujioka et al. | 604/60 |
| 4,955,882 | 9/1990 | Hakky | 606/14 |
| 4,966,597 | 10/1990 | Cosman | 606/50 |
| 4,976,709 | 12/1990 | Sand | 606/5 |
| 4,976,715 | 12/1990 | Bays et al. | 606/77 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,085,657 | 2/1992 | Ben-Simhon | 606/42 |
| 5,098,430 | 3/1992 | Fleenor | 606/42 |
| 5,100,402 | 3/1992 | Fan | 606/41 |
| 5,103,804 | 4/1992 | Abele et al. | 128/4 |
| 5,178,620 | 1/1993 | Eggers et al. | 606/41 |
| 5,186,181 | 2/1993 | Franconi et al. | 128/804 |
| 5,191,883 | 3/1993 | Lennox et al. | 128/401 |
| 5,192,267 | 3/1993 | Shapira et al. | 604/22 |
| 5,201,729 | 4/1993 | Hertzmann et al. | 606/2 |
| 5,201,730 | 4/1993 | Easley et al. | 606/4 |
| 5,201,731 | 4/1993 | Hakky | 606/15 |
| 5,213,097 | 5/1993 | Zeindler | 128/401 |
| 5,230,334 | 7/1993 | Klopotek | 128/399 |
| 5,242,439 | 9/1993 | Larsen et al. | 606/15 |
| 5,242,441 | 9/1993 | Avitall | 606/41 |
| 5,261,906 | 11/1993 | Pennino et al. | 606/46 |
| 5,267,994 | 12/1993 | Gentelia et al. | 606/15 |
| 5,275,151 | 1/1994 | Shockey et al. | 128/4 |
| 5,284,479 | 2/1994 | de Jong | 604/60 |
| 5,304,169 | 4/1994 | Sand | 606/5 |
| 5,308,311 | 5/1994 | Eggers et al. | 606/28 |
| 5,311,858 | 5/1994 | Adair | 128/4 |
| 5,320,115 | 6/1994 | Kenna | 128/898 |
| 5,323,778 | 6/1994 | Kandarpa et al. | 128/653.2 |
| 5,334,193 | 8/1994 | Nardella | 606/41 |
| 5,342,357 | 8/1994 | Nardella | 606/40 |
| 5,348,554 | 9/1994 | Imran et al. | 606/41 |
| 5,352,868 | 10/1994 | Denen et al. | 219/501 |
| 5,354,331 | 10/1994 | Schachar | 623/4 |
| 5,364,395 | 11/1994 | West, Jr. | 606/46 |
| 5,366,443 | 11/1994 | Eggers et al. | 604/114 |
| 5,366,490 | 11/1994 | Edwards et al. | 607/99 |
| 5,382,247 | 1/1995 | Cimino et al. | 606/33 |
| 5,397,304 | 3/1995 | Truckai | 604/95 |
| 5,401,272 | 3/1995 | Perkins | 606/15 |
| 5,415,633 | 5/1995 | Lazarus et al. | 604/95 |
| 5,423,806 | 6/1995 | Dale et al. | 606/15 |
| 5,433,739 | 7/1995 | Sluijter et al. | 607/99 |
| 5,437,661 | 8/1995 | Rieser | 606/15 |
| 5,437,662 | 8/1995 | Nardella | 606/40 |
| 5,451,223 | 9/1995 | Ben-Simhon | 606/42 |
| 5,458,596 | 10/1995 | Lax et al. | 606/31 |
| 5,465,737 | 11/1995 | Schachar | 128/898 |
| 5,484,403 | 1/1996 | Yoakum et al. | 604/59 |
| 5,484,432 | 1/1996 | Sand | 606/5 |
| 5,484,435 | 1/1996 | Fleenor et al. | 606/46 |
| 5,487,757 | 1/1996 | Truckai et al. | 607/122 |
| 5,498,258 | 3/1996 | Hakky et al. | 606/15 |
| 5,500,012 | 3/1996 | Brucker et al. | 607/122 |
| 5,507,812 | 4/1996 | Moore | 623/13 |
| 5,514,130 | 5/1996 | Baker | 606/41 |
| 5,524,338 | 6/1996 | Martyniuk et al. | 29/825 |
| 5,527,331 | 6/1996 | Kresch et al. | 606/170 |
| 5,542,920 | 8/1996 | Cherif Cheikh | 604/57 |
| 5,569,242 | 10/1996 | Lax et al. | 606/42 |
| 5,599,356 | 2/1997 | Edwards et al. | 606/41 |
| 5,630,839 | 5/1997 | Corbett, III et al. | 607/137 |
| 5,681,282 | 10/1997 | Eggers et al. | 604/114 |
| 5,683,366 | 11/1997 | Eggers et al. | 604/114 |
| 5,688,270 | 11/1997 | Yates et al. | 606/51 |
| 5,697,909 | 12/1997 | Eggers et al. | 604/114 |
| 5,718,702 | 2/1998 | Edwards | 606/41 |
| 5,728,795 | 3/1998 | Bays | 606/22 |
| 5,810,809 | 8/1998 | Rydell | 606/49 |

FOREIGN PATENT DOCUMENTS

| | | | |
|---|---|---|---|
| 0 542 412 A1 | 5/1993 | European Pat. Off. | A61B 17/39 |
| 0 558 297 A2 | 9/1993 | European Pat. Off. | A61M 25/00 |
| 0 566 450 A1 | 10/1993 | European Pat. Off. | A61N 5/02 |
| 0 572 131 A1 | 12/1993 | European Pat. Off. | A61B 17/39 |
| 0 682 910 A1 | 11/1995 | European Pat. Off. | A61B 1/00 |
| 0 479 482 B1 | 5/1996 | European Pat. Off. | A61B 17/39 |
| 0 729 730 A1 | 9/1996 | European Pat. Off. | A61B 17/32 |
| 0 737 487 A2 | 10/1996 | European Pat. Off. | A61M 25/01 |
| 0 783 903 A1 | 7/1997 | European Pat. Off. | A61N 5/04 |
| 1122634 | 9/1956 | France . | |
| 2 645 008 | 10/1990 | France | A61B 17/32 |
| 3511107A1 | 10/1986 | Germany | A61B 17/39 |
| 3632197 A1 | 3/1988 | Germany | A61B 10/00 |
| 39 18316 | 3/1990 | Germany | A61B 17/39 |
| 5-42166 | 5/1993 | Japan | A61B 17/39 |
| 637118 | 12/1978 | Russian Federation | A61B 17/18 |
| 1 340 451 | 12/1973 | United Kingdom | A61F 1/00 |
| 2 164 473 | 3/1986 | United Kingdom | A61B 17/36 |
| WO 82/02488 | 8/1982 | WIPO | A61B 17/39 |
| WO 85/02762 | 7/1985 | WIPO | A61B 17/36 |
| WO 92/10142 | 6/1992 | WIPO | A61B 17/36 |
| WO 93/01774 | 2/1993 | WIPO | A61F 7/12 |
| WO 93/16648 | 9/1993 | WIPO | A61B 17/32 |
| WO 93/20984 | 10/1993 | WIPO | B26D 1/11 |
| WO 95/01814 | 1/1995 | WIPO | A61N 5/02 |
| WO 95/10981 | 4/1995 | WIPO | A61B 8/12 |
| WO 95/13113 | 5/1995 | WIPO | A61N 5/02 |
| WO 95/18575 | 7/1995 | WIPO | A61B 17/39 |

| | | | |
|---|---|---|---|
| WO 95/20360 | 8/1995 | WIPO | A61B 17/39 |
| WO 95/25471 | 9/1995 | WIPO | A61B 17/39 |
| WO 95/30373 | 11/1995 | WIPO | A61B 17/00 |
| WO 96/11638 | 4/1996 | WIPO | A61B 17/32 |
| WO 96/34568 | 11/1996 | WIPO | A61B 17/36 |
| WO 96/39914 | 12/1996 | WIPO | A61B 1/00 |
| WO 97/06855 | 2/1997 | WIPO | A61N 1/40 |
| WO 98/07468 | 2/1998 | WIPO | A61N 1/40 |

OTHER PUBLICATIONS

Houpt, J. et al., "Experimental Study of Temperature Distributions and Thermal Transport During Radiofrequency Current Therapy of the Intervertebral Disc", *Spine,* vol. 21, No. 15, (1996), pp. 1808–13.

Troussier, B. et al., "Percutaneous Intradiscal Radio–Frequency Thermocoagulation: A Cadaveric Study", *Spine,* vol. 20, No. 15, (Aug. 1995), pp. 1713–18.

Beadling, L., "Bi–Polar electrosurgical devices: Sculpting the future of arthroscopy", *Orthopedics today,* vol. 17, No. 1, Jan. 1997, 4 pages.

Ellman International Mfg., Inc., 1989, Catalog, pp. 1–15, 20.

Cosset, J.M., Resistive Radiofrequency (Low Frequency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

«6,004,320»

CLIP ON ELECTROCAUTERIZING SHEATH FOR ORTHOPEDIC SHAVE DEVICES

BACKGROUND OF THE INVENTION

Relationship to Copending Application

This application is a Utility Application which claims priority to Provisional application Ser. No. 60/059,383, [Attorney Docket No. 17616.725], entitled *Electrocauterizing Sheath for Arthroscopic Shave Device* filed on: Sep. 19, 1997. This application is related to Utility application, Ser. No. 09/066,615, [Attorney Docket No. 17616.786], entitled *Electrocauterizing Tool for Orthopedic Shave Devices* filed on: Apr. 24, 1998; and Utility application, Ser. No. 09/034,885, [Attorney Docket No. 17616.798], entitled *Electrocauterizing TIP for Orthopedic Shave Devices* filed on: Mar. 4, 1998, all of which are incorporated herein by reference.

FIELD OF THE INVENTION

This invention relates to improved surgical and cauterizing apparatus and methods for their use.

DESCRIPTION OF RELATED ART

Arthroscopic surgery is becoming increasingly popular, because it generally does less damage than open procedures, produces less scarring in and around joints, and results in faster healing and return of the patient to full productivity.

Nevertheless, arthroscopic surgery has its limitations. The surgeon must operate through a narrow tube formed in the body on which surgery is being carried out, which is awkward. Only one probe can be used at a time for many operations. Often the viewing camera is positioned at an angle different from the surgeon's normal gaze. This contrasts with "open surgery" where the surgeon has relative ease of viewing the surgical site and can freely move both hands.

Occasionally, during the performance of an arthroscopic or similar minimally invasive procedure, a surgeon will penetrate a vessel within the surgical site. At this point, the surgeon may desire to cauterize the vessel.

One way of cauterizing the vessel is the use of radio frequency (RF) energy, as described in U.S. Pat. No. 5,100,402 to Fan. Such RF methods offer a quick and relatively easy way of cauterizing penetrated vessels. However, use of current RF cauterizing devices usually requires the surgeon to withdraw the surgical tool being used at the time, and insert a tool for cauterizing the penetrated vessel. This switching of the tools is usually required because of the space limitations involved in arthroscopic surgery.

This switching of tools during surgery can be time consuming, awkward, and potentially dangerous to the patient. Additionally, there is the danger of not being able to locate the penetrated vessel. Therefore, there is the need for an improved surgical and cauterizing apparatus and methods for using the apparatus to avoid the above-mentioned problems.

SUMMARY OF THE INVENTION

In one embodiment, the invention is directed to an integrated surgical and cauterizing apparatus, comprising a surgical instrument including a drive member, a cannula, and a tool, and the cannula attached at a proximal end to the drive member and defining at a distal end thereof an opening, and the tool including a shaft and a tip, and the shaft contained within the cannula and connecting the tip in the opening of the cannula to the drive member to produce a surgical motion of the tip; and a cauterizing instrument comprising a first electrode, and a first conductor, and the first electrode affixed to the cannula adjacent to the distal end of the cannula and the first conductor providing an electrical path from the first electrode for application of electrical power to the first electrode to produce a cauterizing effect.

In another embodiment, the invention is directed to a cauterizing instrument for attachment to a surgical instrument, and the surgical instrument including a cannula, and the cauterizing instrument comprising a first electrode, affixed to the cannula adjacent to a distal end of the cannula; and a first conductor providing an electrical path from the first electrode for application of electrical power to the first electrode to produce a cauterizing effect.

In yet another embodiment, the invention is directed to a method of performing a surgical procedure, comprising use of the integrated surgical and cauterizing apparatus as described above in connection with the procedure.

DETAILED DESCRIPTION OF THE INVENTION

FIGS. 1–8 show alternate embodiments of a cauterizing apparatus for attachment to a surgical instrument. The ability of these embodiments to be interfaced with existing surgical instruments reduces the time, awkwardness and potential danger to the patient that is associated with separate surgical and cauterizing instruments of the prior art.

Figure 1:
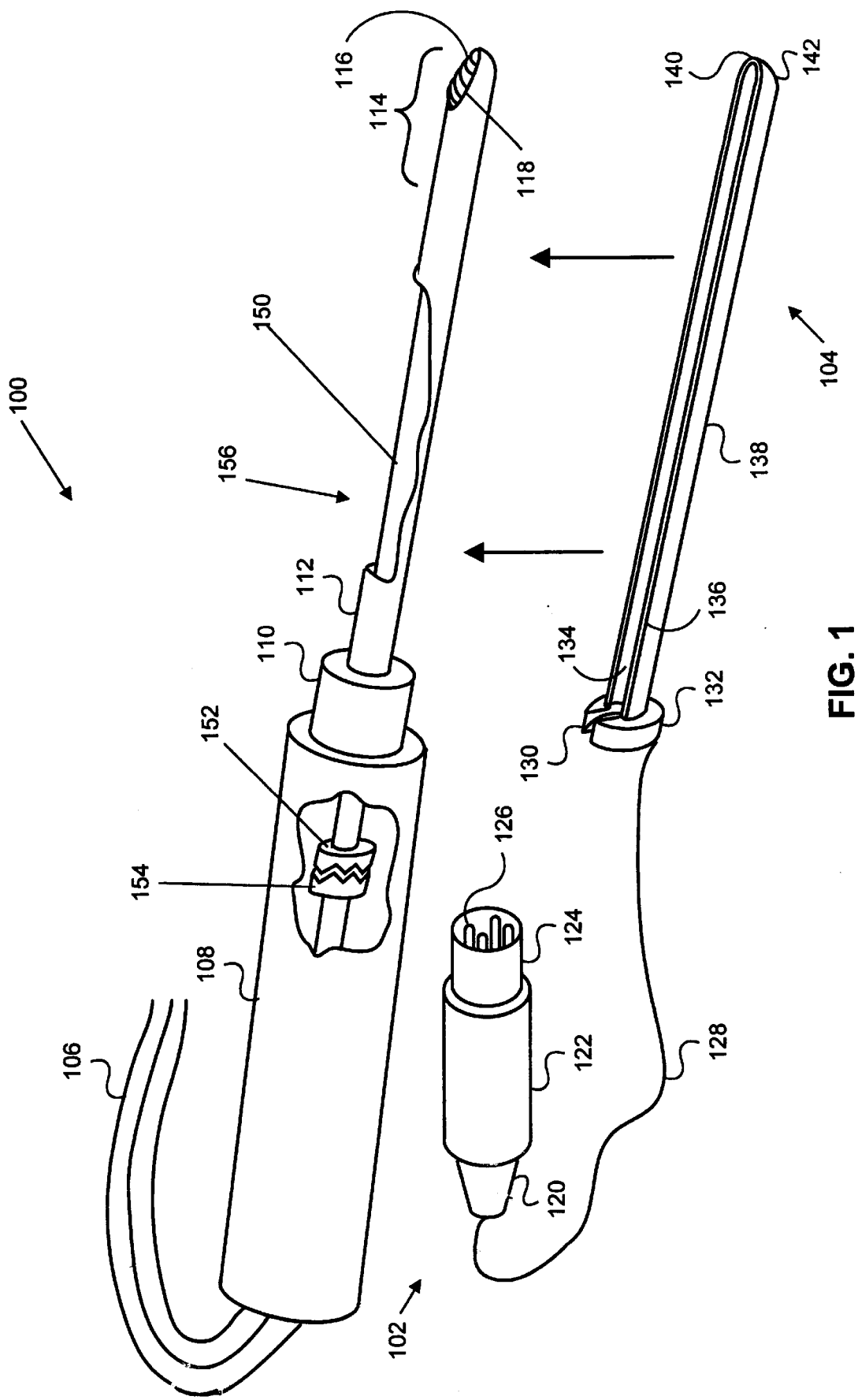
FIG. 1 is an isometric view of an embodiment of the claimed cauterizing instrument and a surgical instrument.

FIG. 1 shows an embodiment of the invention, including surgical instrument 100, electrical connector 102, and cauterizing instrument 104. Surgical instrument 100 includes power cord 106, handle 108, quick connect 110, cannula 112, tool 156. Handle 108 includes drive member 154. Cannula 112 includes a cannula opening 118 and distal end 114. Tool 156 includes drive coupling 152, shaft 150, and mechanical cutter 116. Electrical connector 102 includes strain reliever 120, connector body 122, connector shield 124, male connector pins 126, and secure insulated connector wire 128. Cauterizing instrument 104 includes notch 130, hub 132, longitudinal opening 134, longitudinal member 136, conductor 138, cap 140, and electrode 142.

In surgical instrument 100, power cord 106 is connected to handle 108 at a first end of the handle. Cannula 112 is connected at its proximal end to the other end of the handle 108 by quick connect 110. Cannula 112 defines at its distal end 114 cannula opening 118. The mechanical cutter 116 is located within cannula opening 118. The mechanical cutter 116 is connected via shaft 150 to drive member 154 by drive coupling 152. Shaft 150 is contained within cannula 112. Mechanical cutter 116 may be rotated, reciprocated, or moved in a combination of rotation and reciprocation, to produce surgically desired motion, if needed.

It should be noted that the surgical motion in this or any of the embodiments of this invention, can be, for example, rotary, reciprocal, rotary-reciprocal, etc. The shaft and cannula can be straight, or can include an arcuate section. In those instances where the the surgical tool contains an arcuate section, the shaft may contain a flexible section to accomodate the motion of the shaft.

Longitudinal member 136 of the cauterizing instrument 104 is generally arcuate in cross-sectional shape, and subsumes an arc greater than about 180 degrees in cross section. Longitudinal member 136 defines a longitudinal opening 134 between arcuate ends. Opening 134 runs along the longitudinal axis of the longitudinal member, and is shaped complementarily to the outer surface of cannula 112. Cap 140 is present on a distal end of longitudinal member 136. Hub 132 is located on a proximal end of longitudinal member 136. Notch 130 is formed in hub 132 such that it aligns with the longitudinal opening 134. Electrode 142 is located on an exterior surface of cap 140. Electrode 142 is connected to conductor 138 which extends the length of the longitudinal member. The conductor is connected to insulated connector wire 128. Electrical connector 102 has at one end male connector pins 126 and connector shield 124. These are electrically connected through connector body 122 and strain reliever 120 to insulated connector wire 128.

To assemble cauterizing instrument 104 and surgical instrument 100 into a combination, cauterizing instrument 104 is placed on cannula 112, in such a way that notch 130 is aligned with the proximal end of the cannula 112, and cap 140 is aligned with the distal end 114 of the cannula 112. In this position, mechanical cutter 116 is exposed, and the electrode 142 is positioned adjacent the mechanical cutter 116.

In operation, the surgical apparatus of surgical instrument 100 and cauterizing instrument 104 functions to allow mechanical cutter 116 to be exposed through distal end 114 of cannula 112 so as to provide mechanical cutting action at a desired surgical site. On occasion, a surgeon operating a surgical apparatus in an arthroscopic procedure, for example, may open a vessel in or near the surgical site that then must be cauterized. As discussed above, before the present invention was available, the surgeon would have to remove the surgical apparatus, insert a cauterizing instrument and then re-insert the surgical apparatus. However, by using the surgical apparatus of the present invention, a surgeon may align the surgical apparatus and bring the electrode into alignment with the desired surgical site. The surgeon may then provide power to electrode 142 through electrical connector 102, thus exposing the surgical site to radio frequency energy sufficient to cauterize the surgical site. The surgeon can then resume the minimally invasive surgical procedure, such as arthroscopy or other such procedures.

Electrical power can be supplied in at least one of two ways. First, power can be supplied using the monopolar configuration shown in FIG. 1. In a monopolar configuration, a power supply supplies energy through electrical connector 102 to electrode 142. A return path for the energy is provided by a body grounding pad that attaches a surface of a patient to the power supply.

Additionally, electrical power can be supplied in a bipolar configuration. In a bipolar configuration, a second electrode is positioned on cap 140 adjacent to electrode 142. Both electrodes are connected via conductors to electrical connector 102. Power supplied to these electrodes provides a cauterizing current between the electrodes.

Figure 2:
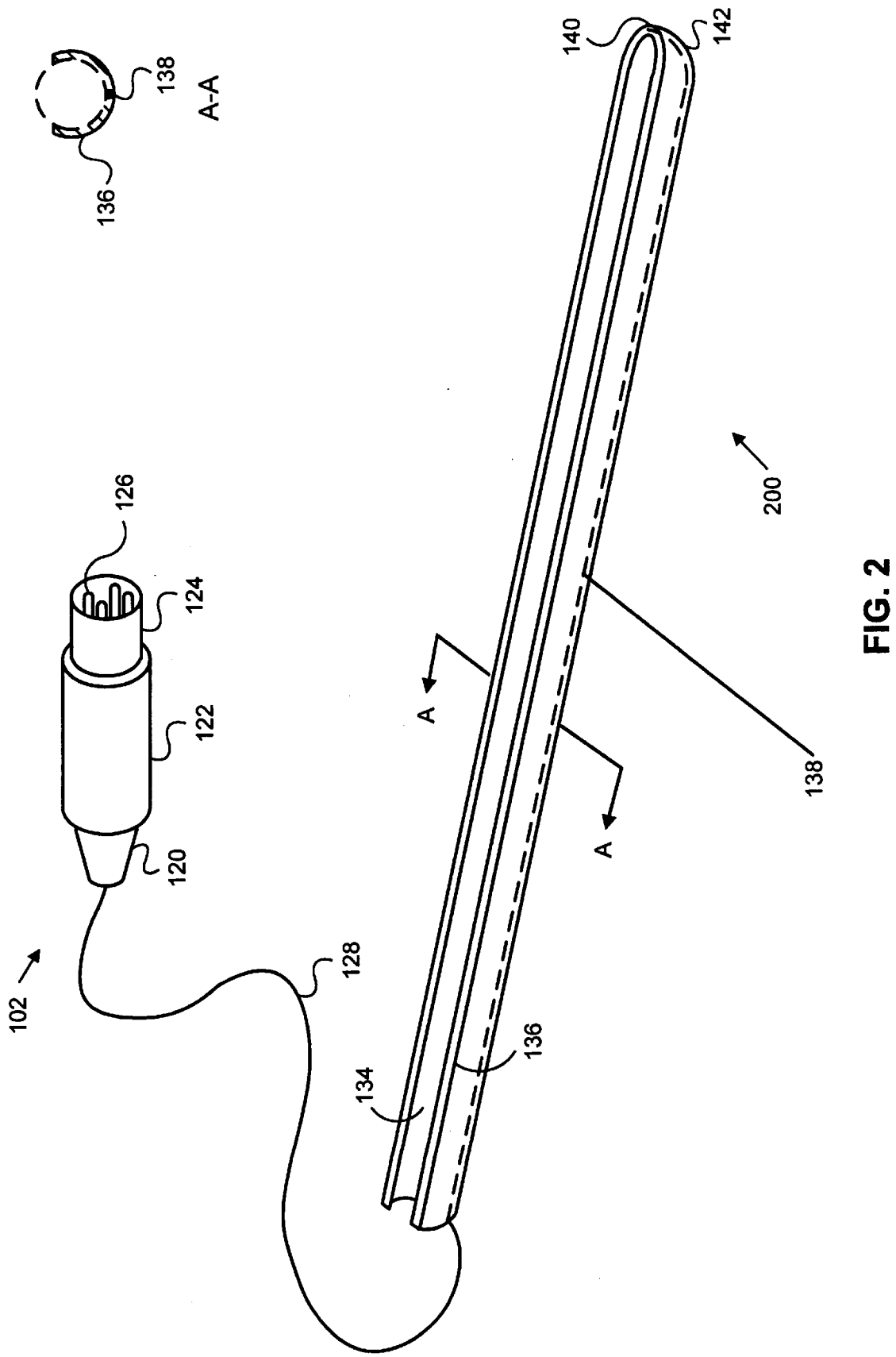
FIG. 2 is an isometric view of an embodiment of the cauterizing instrument, together with a cross-sectional view, taken through a central portion thereof.

FIG. 2 shows an alternative embodiment of the invention. This embodiment includes electrical connector 102 and cauterizing instrument 200. Cauterizing instrument 200 includes longitudinal member 136, conductor 138, cap 140, and electrode 142. Cauterizing instrument 200 is shown in cross section in A—A, which is taken from a central portion of the cauterizing instrument 200. Electrical connector 102 includes insulated connector wire 128, strain reliever 120, connector body 122, connector shield 124 and male connector pins 126.

Longitudinal member 136 is generally arcuate in cross-sectional shape, and subsumes an arc greater than about 180 degrees in cross section. Longitudinal member 136 includes at a distal end thereof cap 140. A longitudinal opening 134 is defined by the longitudinal member 136 and extends from the cap 140 at the distal end of the longitudinal member to the proximal end of the longitudinal member.

Electrode 142 is located on an exterior surface of cap 140. Electrode 142 is connected to conductor 138 which extends the length of the longitudinal member 136. The conductor is connected to insulated connector wire 128. Electrical connector 102 has at one end male connector pins 126 and connector shield 124. These are electrically connected through connector body 122 and strain reliever 120 to insulated connector wire 128. As shown in cross section A-A, conductor 138 is embedded in longitudinal member 136.

In operation, electrical power is supplied through electrical connector 102 to conductor 138 in longitudinal member 136. Power is thus supplied to electrode 142, causing electrode 142 to emit radio frequency radiation at a desired surgical site, to provide the desired cauterizing effect.

Figure 3:
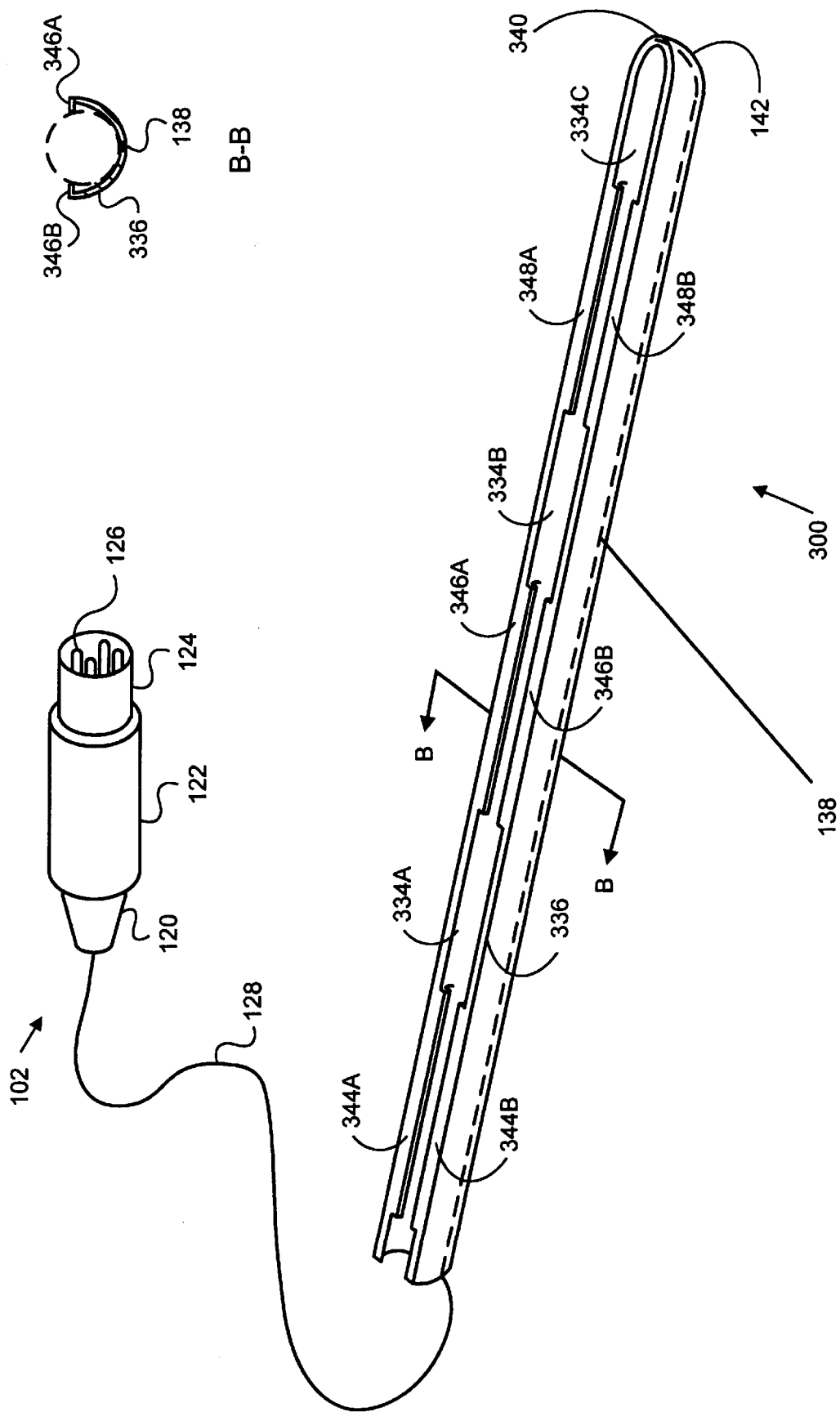
FIG. 3 is an isometric view of another embodiment of a cauterizing instrument, together with a cross-sectional view, taken through a central portion thereof.

FIG. 3 shows an embodiment of the invention featuring an alternative way of securing the cauterizing instrument. FIG. 3 includes electrical connector 102 and cauterizing instrument 300. Cauterizing instrument 300 includes longitudinal member 336; longitudinal openings 334A–B; conductor 138; opposing tabs 344A–B, 346A–B, and 348A–B; cap 340; and electrode 142. Cauterizing instrument 200 is shown in cross section in B—B. Electrical connector 102 includes insulated connector wire 128, strain reliever 120, connector body 122, connector shield 124 and male connector pins 126.

Longitudinal member 336 is generally arcuate in cross-sectional shape, and subsumes an arc greater than about 180 degrees in cross section. Longitudinal member 336 has a series of opposing tabs 344A–B, 346A–B, and 348A–B running along the edges of its arcuate section. These tabs and the edges of the longitudinal member 336 define a series of longitudinal openings 334A–B. At the distal end of longitudinal member 336, an opening 334C is defined by the cap, the arcuate cross section and opposing tabs 348A–B. The whole of cauterizing instrument 300 is shaped complementarily to the outer surface of a cannula so that the opposing tabs and other structures of the cauterizing instrument 300 serve to frictionally secure cauterizing instrument 300 in place against the cannula.

Electrode 142 is located on an exterior surface of cap 140. Electrode 142 is connected to conductor 138 which extends the length of the longitudinal member 136. The conductor is connected to insulated connector wire 128. The electrical connection of the insulated connector wire to the electrical connector 102 is identical to that discussed above. As shown in cross section B—B, opposing tabs 346A–B clamp an external surface of the cannula 112. Conductor 138 is embedded in longitudinal member 336 in this embodiment. As will be obvious to those skilled in the art, conductor 138 could alternately be affixed to an exterior surface of the longitudinal member. Alternately conductor 138 could be sandwiched between an interior surface of the longitudinal member 336 and an exterior surface of the cannula.

In operation, electrical power is supplied through electrical connector 102 to conductor 138 present in longitudinal member 136. Power is thus supplied to electrode 142, causing electrode 142 to emit radio frequency radiation, the effects of which have been described above.

Figure 4:
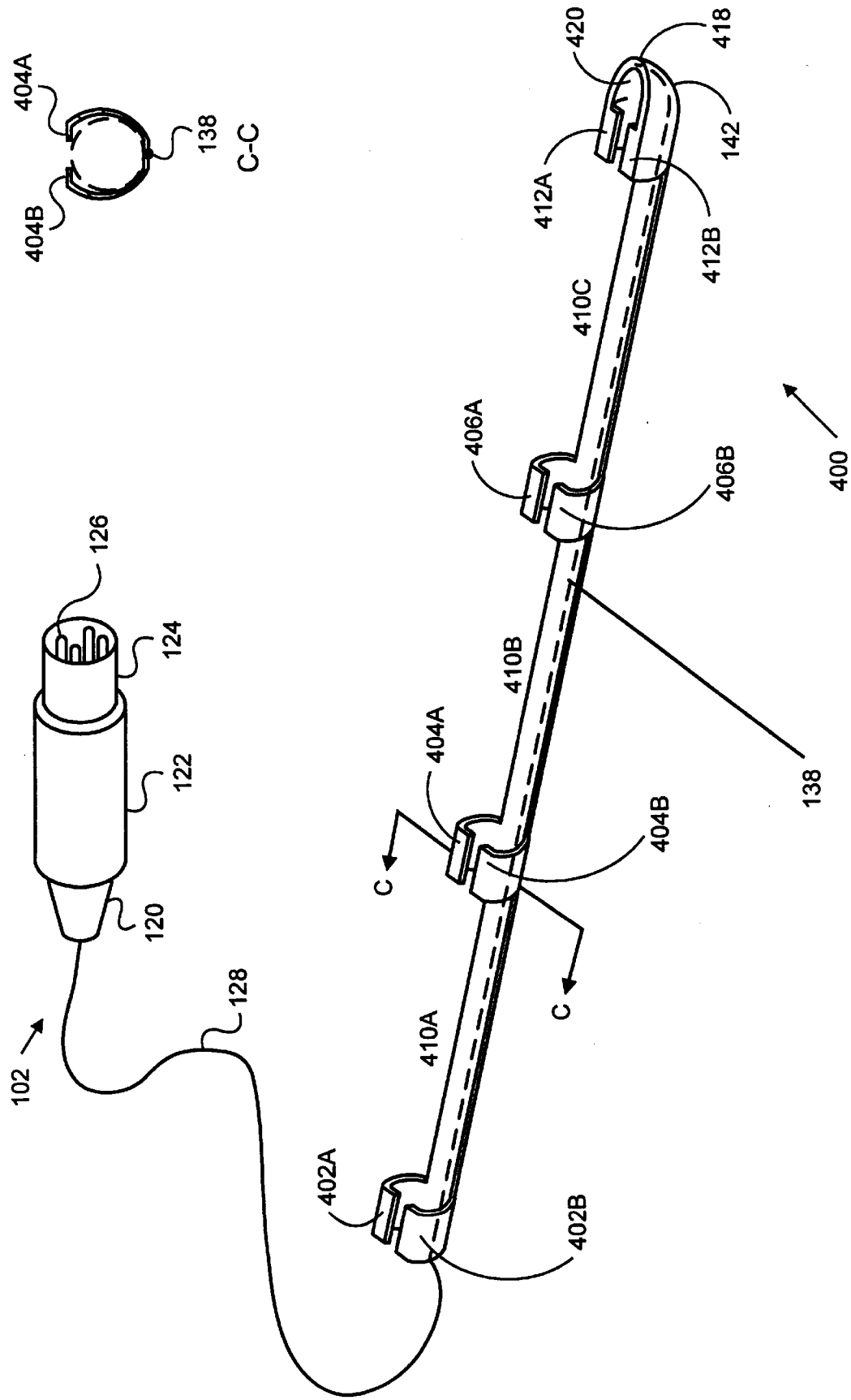
FIG. 4 is an isometric view of an embodiment of a cauterizing instrument, together with a cross-sectional view, taken through a central portion thereof

FIG. 4 shows an embodiment of the invention having a cauterizing piece with a reduced amount of material. Shown are electrical connector 102 and cauterizing instrument 400. Electrical connector 102 has been described above. Cauterizing instrument 400 includes longitudinal members 410A–B–C with proximal end tabs 402A–B; intermediate tabs 404A–B, 406A–B, and distal end tabs 412A–B. Also present on cauterizing instrument 400 are electrode 142, cap 418, and an opening for mechanical cutter 420. Cauterizing instrument 400 is shown in cross section at points C—C, taken through intermediate tab 404A–B.

Cauterizing instrument 400 has along its longitudinal axis longitudinal members 410A–B–C; with proximal end tabs 402A–B present at the proximal end of the cauterizing piece; intermediate tabs 404A–B, and 406A–B present at intermediate points along the longitudinal axis of cauterizing instrument 400. Cap 418 is present at the distal end of cauterizing instrument 400, and defines distal end tabs 412A–B together with an opening for mechanical cutter 420. Electrode 142 is present on cap 418. Running along the longitudinal axis of cauterizing instrument 400 is conductor 138, connected at its proximal end to insulated connector wire 128 and at the distal end to electrode 142. The connection between secure insulated connector wire 128 and electrical connector 102 has been described above. Cross section C—C shows opposing intermediate tabs 404A–B clamping an external surface of the cannula Conductor 138 is shown embedded in the longitudinal member.

In operation cauterizing instrument 400 receives power from electrical connector 102, whereby electrode 142 is energized to emit radio frequency energy, with the results described above.

Figure 5:
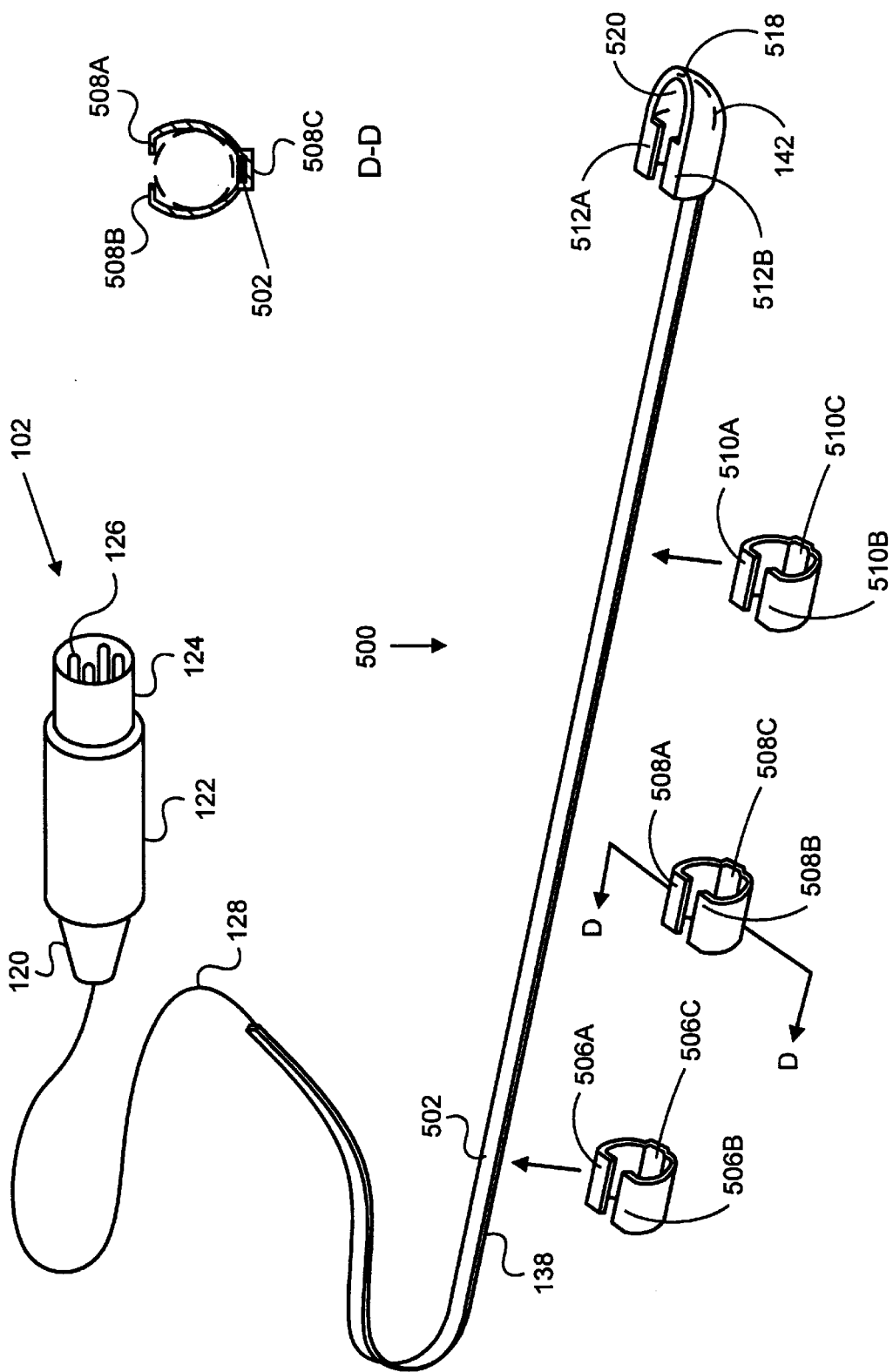
FIG. 5 is an isometric view of an embodiment of a cauterizing instrument, together with a cross-sectional view, taken through a central portion thereof.

FIG. 5 shows an embodiment of the invention with a very flexible configuration, including electrical connector 102, and cauterizing instrument 500. Electrical connector 102 has been described above. Cauterizing instrument 500 includes longitudinal member 502, and clamps 506–510. Longitudinal member 502 includes conductor 138, cap 518, and electrode 142. Cap 518 is present at the distal end of cauterizing instrument 500 and defines distal end tabs 512A–B, and an opening for mechanical cutter 520. Clamps 506–510 each include opposing tabs 506A–B, 508A–B, and 510A–B; each tab having recessed slots 506C–510C. Clamp 508 and longitudinal member 502 is shown in cross section at elevation D—D, taken through a central portion thereof.

Longitudinal member 502 includes at its distal end cap 518. The cap is generally arcuate in cross-section, and has distal end tabs 512A–B, and an opening for mechanical cutter 520. Disposed along the length of longitudinal member 502 are clamps 506, 508, and 510 having tabs 506A–B, 508A–B, and 510A–B, respectively. Each of the clamps may have a recessed slot 506C–510C for locating the longitudinal member. Each clamp is dimensioned to clamp the longitudinal member to an external surface of a cannula.

Electrode 142 is located on an exterior surface of the cap. The electrode 142 is connected to conductor 138 at the distal end of the longitudinal member. Conductor 138 runs the length of longitudinal member 502. Conductor 138 is connected at its proximal end to insulated connector wire 128. Insulated connector wire 128 is connected to electrical connector 102 in the manner described above. In cross section D—D, opposing tabs 508A–B are shown clamping an exterior surface of a cannula. Slot 508C locates the longitudinal member 502 to the exterior surface of the cannula.

In operation, clamps 506–510 operate to secure the longitudinal member to a cannula of a surgical instrument. Power may then be supplied through electrical connector 102 to energize electrode 142, in the manner described above.

Figure 6:
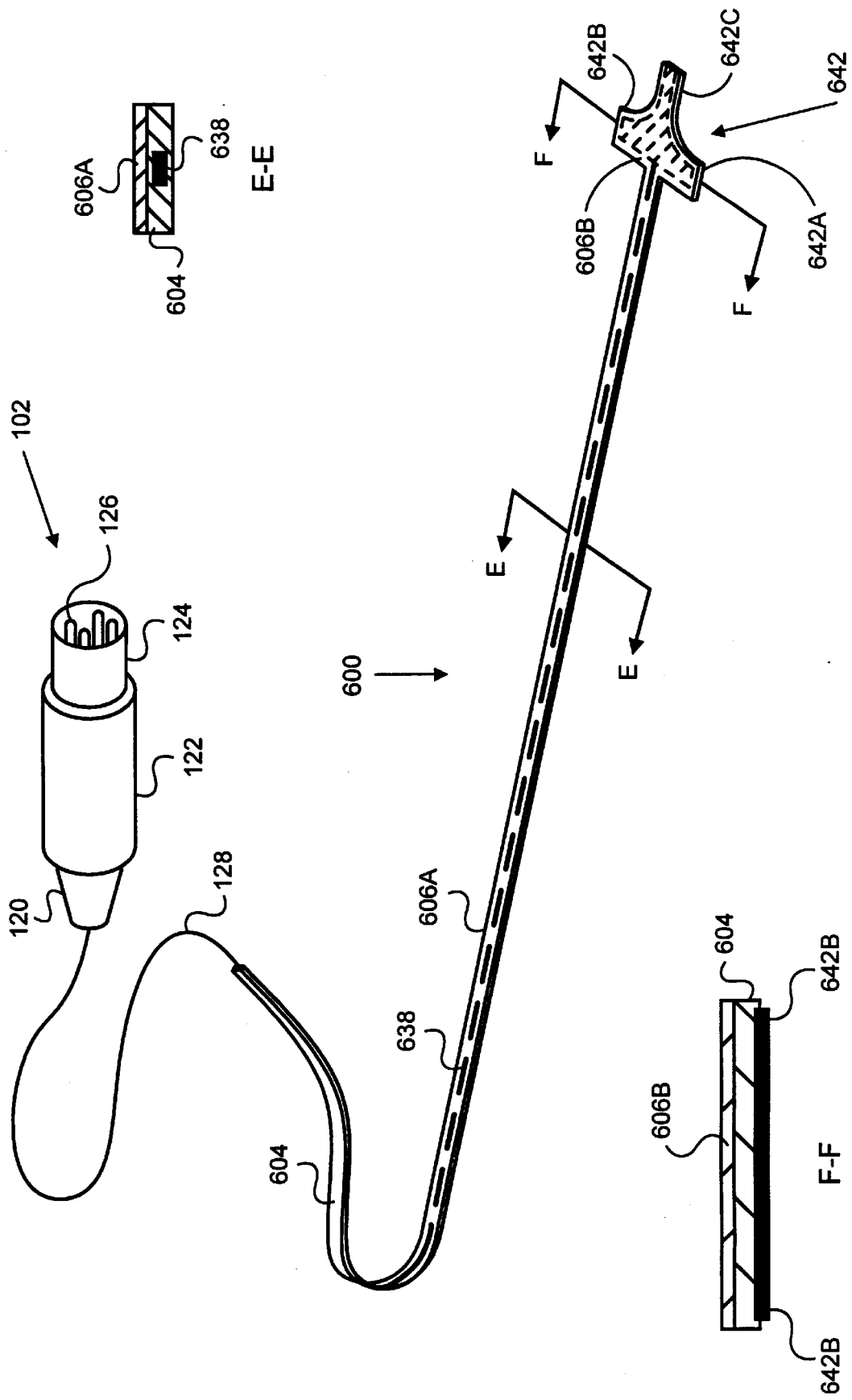
FIGS. 6–7 are isometric views of another embodiment of the cauterizing instrument and a surgical instrument, together with cross-sectional views of the cauterizing instrument.
Figure 7:
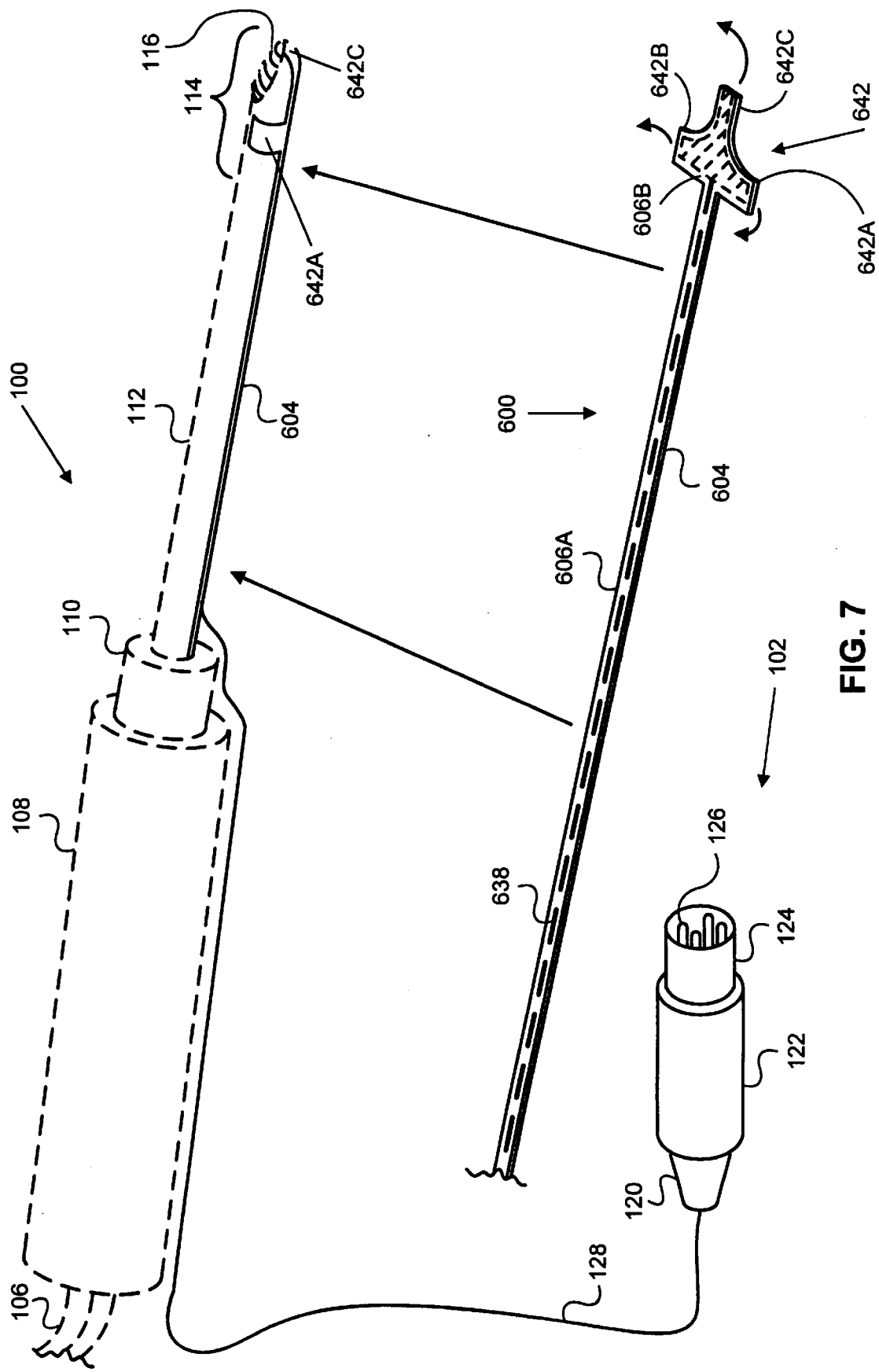

FIGS. 6–7 show an embodiment of the invention that is easily adaptable to variously shaped cannulas. FIGS. 6 and 7 include electrical connector 102 and cauterizing instrument 600. Cauterizing instrument 600 includes longitudinal member 604, which contains ribbon conductor 638, bonding strip 606A, bonding pad 606B, and electrode 642. Electrode 642 includes transverse tabs 642A–B and distal end tab 642C. Electrical connector 102 has been described above.

Longitudinal member 604 of cauterizing instrument 600 includes on a lower surface at its distal end an electrode generally 642. [See cross section F—F]. On an opposing surface, at said distal end, a bonding pad 606B is attached to the longitudinal member 604. [See cross section F—F]. Along the length of the longitudinal member, a bonding strip 606A is located. Electrode 642 is attached to insulated connector wire 128 via conductor 638. As shown in cross section E—E, conductor 638 is embedded within longitudinal member 604, and bonding strip 606A is attached to longitudinal member 604. Bonding strip 606A is present on an upper portion of longitudinal member 604. This arrangement is shown in cross section E—E, taken through a central portion of longitudinal member 604.

In assembly, as shown in FIG. 7, the proximal end of the longitudinal member 604 is aligned with the proximal end of cannula 112. The bonding pad 606B is aligned with the distal end 114 of cannula 112. Longitudinal member 604 is affixed to cannula 112 using bonding strip 606A. Transverse and distal tabs 642A–B–C are wrapped around distal end 114 of cannula 112, and are securely affixed to the distal end 114 by bonding pad 606B. Mechanical cutter 116 is left exposed, so that it may be used in accordance with the normal operation of surgical instrument 100.

It should be noted that the conductor can be constructed in several different ways. While the embodiment illustrated in FIGS. 6–7 emphaszes adhering the conductor to the cannula using bonding strips, etc., it is within the scope of the invention to construct the conductor using, for example, direct deposition or direct solvent coating of the conductor. Equivalent methods for providing the conductor are within the scope of the invention.

In operation, electrode 642 is energized via electrical connector 102 to accomplish cauterizing of the desired surgical site.

As would be obvious to one of skill in the art, the conductor, discussed above in FIGS. 6–7 as being adhesively bonded to the cannula, could alternatively be thermally bonded to an exterior surface of the cannula. In still another embodiment, the conductor and electrode could be direct deposited on the exterior of the cannula using methods such as vacuum deposition. In this alternative embodiment, an insulating layer would be deposited on the conductor.

Figure 8:
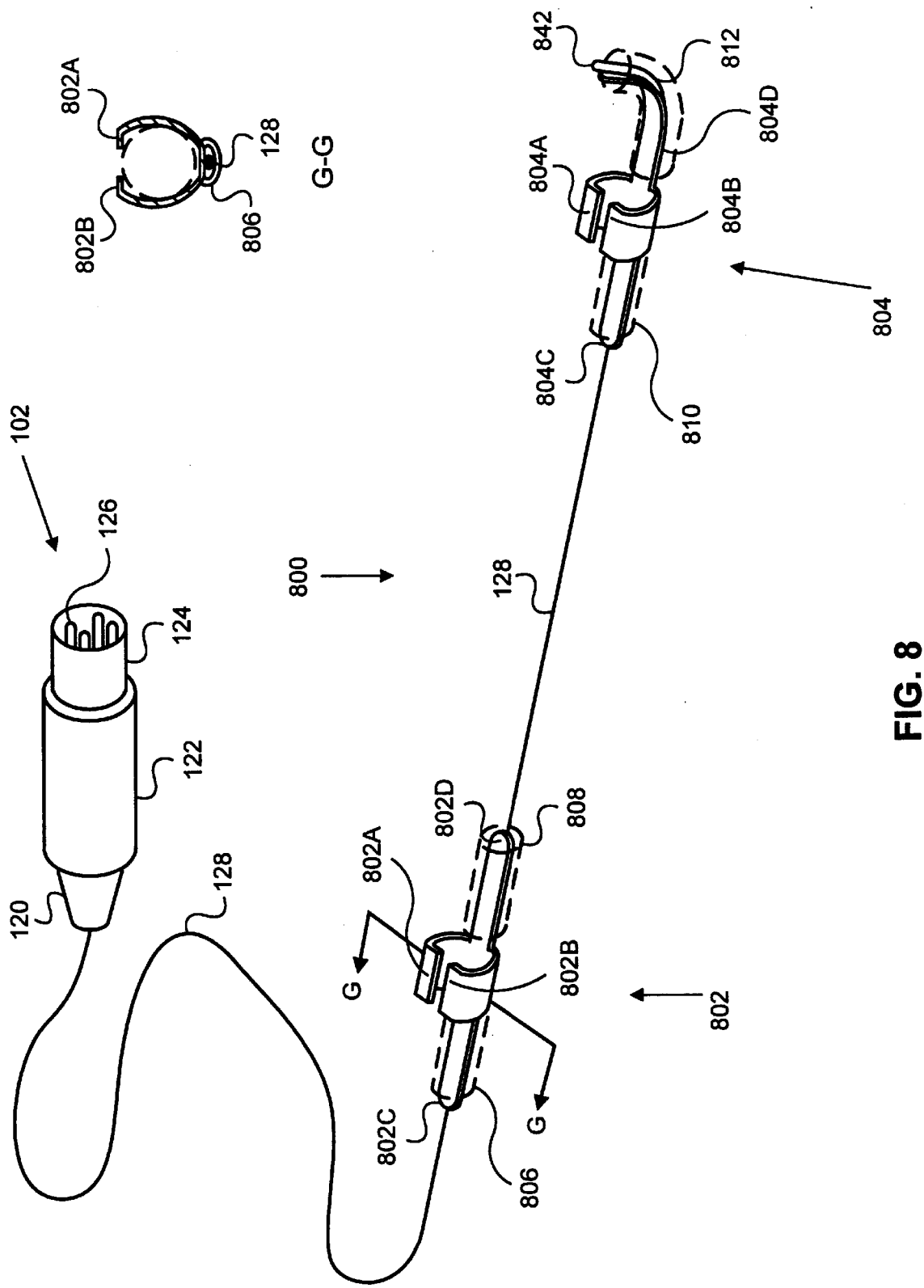
FIG. 8 are isometric views of another embodiment of the cauterizing instrument, and a cross-sectional view thereof.

FIG. 8 shows an embodiment of the invention with a minimum of support material including electrical connector 102 and cauterizing instrument 800. Electrical connector 102 has been described above. Cauterizing instrument 800 includes intermediate clamp 802, insulated connector wire 128, and a distal clamp 804. Intermediate clamp 802 includes heat shrink tubing 806–808. Distal clamp 804 includes heat shrink tubing 810–812 and electrode 842.

Clamp 802 of cauterizing instrument 800 is located distantly from electrode 842. Clamp 804 is located adjacent to electrode 842. Electrode 842 is connected to electrical connector 102 via insulated connector wire 128. Clamp 802 includes opposing tabs 802A–B dimensioned to clamp an external surface of a cannula [see cross section G—G]. Longitudinal tabs 802C–D are included in clamp 802 and extend along an axis parallel to the insulated connector wire 128. Insulated heat shrink tubing 806–808 affix the secure insulated connector wire 128 to the longitudinal tabs [see cross-section G—G]. Distal clamp 804 includes opposing tabs 804A–B dimensioned to clamp a distal end of a cannula. Longitudinal tabs 804C–D are included in distal clamp 804 and extend along an axis parallel to the insulated connector wire 128. Insulated heat shrink tubing 810–812 affix the secure insulated connector wire 128 to the longitudinal tabs 804C–D. Longitudinal tab 804D has an arcuate shape to conform to the distal end of a surgical catheter. Electrode 842 is located at distal end of longitudinal tab 804D and includes an exposed section extending beyond heat shrink tubing 812.

In assembly, cauterizing instrument 800 is attached to the cannula of a surgical instrument, and held in place via opposing tabs 802A–B and 804A–B, which are aligned, respectively, with the proximal and distal ends of the cannula. Longitudinal tabs 802C–D and heat shrink tubing 806 and 808 secure insulated connector wire 128 to clamp 802. Longitudinal tabs 804C–D and heat shrink tubing 810 and 812 secure insulated connector wire 128 to distal clamp 804. Longitudinal tab 804D serves to align electrode 842 with the distal end of a surgical cannula.

In operation, electrical power can be supplied through electrical connector 102 through secure insulated connector wire 128 to electrode 842, thus causing electrode 842 to emit radio frequency energy to produce a cauterizing effect, as has been discussed above.

It will be apparent to those skilled in the art that various modifications and variations can be made in the apparatus and methods of the present invention without departing from the spirit or scope of the invention. Thus, it is intended that the present invention cover the modifications and variations of this invention provided they come within the scope of the appended claims and their equivalents.

What is claimed is:

1. An integrated surgical and cauterizing apparatus, comprising:

a surgical instrument including a drive member, a cannula, and a tool, the cannula being attached at a proximal end to the drive member and defining at a distal end thereof an opening, the tool including a shaft and a tip, the shaft being contained within the cannula and connecting the tip in the opening of the cannula to the drive member to produce a surgical motion of the tip; and a cauterizing instrument comprising a first electrode, a first conductor, a first second clamp dimensioned to affix the first electrode to the cannula, and a second clamp dimensioned to affix the first conductor to the cannula, the first electrode being affixed to the cannula adjacent to the distal end of the cannula and the first conductor providing an electrical path from the first electrode for application of electrical power to the first electrode to produce a cauterizing effect.

2. A cauterizing instrument for attachment to a surgical instrument including a cannula, the cauterizing instrument comprising:

a first electrode adapted to be affixed to the cannula adjacent to a distal end of the cannula;

a first conductor providing an electrical path from the first electrode for application of electrical power to the first electrode to produce a cauterizing effect;

a first clamp dimensioned to clamp the first electrode to the cannula; and a second clamp dimensioned to clamp the first conductor to the cannula.

* * * * *

UNITED STATES PATENT AND TRADEMARK OFFICE
CERTIFICATE OF CORRECTION

PATENT NO.    : 6,004,320
DATED         : December 21, 1999
INVENTOR(S)   : Ramiro L. Reyes, Hugh R. Sharkey and Christopher D. Casscells It is certified that error appears in the above-identified patent and that said Letters Patent is hereby corrected as shown below:

<u>Column 8,</u>
Line 25, change "a first second clamp" to -- a first clamp --

Signed and Sealed this

Eleventh Day of March, 2003

JAMES E. ROGAN
*Director of the United States Patent and Trademark Office*